(12) United States Patent
Feiten et al.

(10) Patent No.: US 9,747,772 B2
(45) Date of Patent: Aug. 29, 2017

(54) MODULAR ASSISTANCE SYSTEM

(71) Applicant: SIEMENS AKTIENGESELLSCHAFT, München (DE)

(72) Inventors: Wendelin Feiten, Neubiberg (DE); Uwe Splettstösser, Ottobrunn (DE)

(73) Assignee: Siemens Aktiengesellschaft, München (DE)

( * ) Notice: Subject to any disclaimer, the term of this patent is extended or adjusted under 35 U.S.C. 154(b) by 210 days.

(21) Appl. No.: 14/356,076

(22) PCT Filed: Oct. 17, 2012

(86) PCT No.: PCT/EP2012/070566
§ 371 (c)(1),
(2) Date: May 2, 2014

(87) PCT Pub. No.: WO2013/064374
PCT Pub. Date: May 10, 2013

(65) Prior Publication Data
US 2014/0313029 A1  Oct. 23, 2014

(30) Foreign Application Priority Data

Nov. 3, 2011 (DE) .......... 10 2011 085 718
Dec. 1, 2011 (DE) .......... 10 2011 087 589

(51) Int. Cl.
*G08B 1/08* (2006.01)
*G08B 21/04* (2006.01)
*G06F 19/00* (2011.01)

(52) U.S. Cl.
CPC ..... *G08B 21/0438* (2013.01); *G06F 19/3406* (2013.01); *G06F 19/3462* (2013.01)

(58) Field of Classification Search
CPC .... A61B 5/0002; G06F 19/3418; G06Q 50/22
(Continued)

(56) References Cited

U.S. PATENT DOCUMENTS 5,590,648 A   1/1997  Mitchell et al.
8,457,713 B2  6/2013  Kagermeier
(Continued)

FOREIGN PATENT DOCUMENTS

DE  102006046689 A1  4/2008
DE  102008010463 A1  8/2009
(Continued)

OTHER PUBLICATIONS

Engelhart K G; An Overview of Health and Human Service Robotics; pp. 205-226; ISSN:0921-8890; DOI:10.1016/0921-8890(89)90046-8; Elsevier Science Publishers; 1989; NL; Nov. 1, 1989.
(Continued)

*Primary Examiner* — George Bugg
*Assistant Examiner* — Anthony D Afrifa-Kyei
(74) *Attorney, Agent, or Firm* — Lempia Summerfield Katz LLC

(57) ABSTRACT

Modular assistance system (1) for a person (4), with at least one mobile unit (2) that has a recognition module (6) for recognizing a functional requirement of the person (4) and provides the function of the person (4) depending on the detected function requirement of the person (4) by means of at least one replaceable function module (7).

20 Claims, 7 Drawing Sheets

(58) Field of Classification Search
USPC .............. 340/539.11, 539.12, 539.14, 573.1; 482/51, 52; 312/240, 294; 600/300, 301; 606/130; 604/318
See application file for complete search history.

(56) References Cited

U.S. PATENT DOCUMENTS

| | | | |
|---|---|---|---|
| 8,505,959 B2* | 8/2013 | Darling, III | A61G 1/013 280/640 |
| 8,509,947 B2 | 8/2013 | Jarisch et al. | |
| 8,786,429 B2* | 7/2014 | Li | G01S 5/02 205/687 |
| 2003/0165373 A1 | 9/2003 | Felder et al. | |
| 2004/0100376 A1* | 5/2004 | Lye | A61B 5/411 340/539.12 |
| 2005/0154265 A1 | 7/2005 | Miro et al. | |
| 2005/0216126 A1 | 9/2005 | Koselka et al. | |
| 2006/0267779 A1* | 11/2006 | Ishikawa | A41D 13/018 340/573.1 |
| 2008/0001735 A1* | 1/2008 | Tran | G06F 19/3418 340/539.22 |
| 2008/0081992 A1 | 4/2008 | Kagermeier | |
| 2009/0108552 A1* | 4/2009 | Mann, III | B64F 1/364 280/79.3 |
| 2009/0319079 A1* | 12/2009 | Arceta | A61G 12/001 700/228 |

FOREIGN PATENT DOCUMENTS

| | | |
|---|---|---|
| EP | 1741044 B1 | 9/2011 |
| JP | 2005046926 A | 2/2005 |
| JP | 2007193736 A | 8/2007 |
| JP | 2010517875 A | 5/2010 |
| WO | WO2007041295 A2 | 4/2007 |

OTHER PUBLICATIONS

German Office Action for German Application No. 10 2011 087 589.1, mailed Sep. 25, 2012, with English Translation.

PCT International Search Report and Written Opinion of the International Searching Authority dated Feb. 5, 2013 for corresponding PCT/EP2012/0770566.

von Stösser, A.: "Roboter als Lösung für den Pflegenotstand? Ethische Fragen", in: Archiv für Wissenschaft und Praxis der sozialen Arbeit Mar. 2011.

Japanese Office Action for Japanese Application No. 2014-540380, mailed May 8, 2015 with English Translation.

* cited by examiner

MODULAR ASSISTANCE SYSTEM

The present application is a §371 nationalization of PCT Application No. PCT/EP2012/070566, filed Oct. 17, 2012, and designating the United States, which, in turn, claims the benefit of DE 10 2011 085 718.4, filed on Nov. 3, 2011, and DE 10 2011 087 589.1, filed on Dec. 1, 2011, the entire disclosures of which are incorporated by reference herein.

BACKGROUND

The present embodiments relate to a modular assistance system for one or more persons within a household.

Conventionally, elderly persons are cared for in their dwellings by health visitor services. A care attendant comes daily or a number of times a day to the dwelling of the person to be cared for and helps with the daily care (e.g., to provide basic requirements). However, a disadvantage of conventional health visitor services is that the care attendants may only have a relatively short amount of time for caring for the respectively affected person. Sufficient care of the affected person in the time intervals between the visits by the care attendant may not be ensured. If a person to be cared for has a need or a functional requirement, the person, in many cases, waits for the next arrival of the care attendant until the person is cared for.

Conventionally, a person to be cared for has a number of different needs or different requirements of functions (e.g., the supply of drinks and food), the operation of technical household and entertainment appliances (e.g., television or radio), and the operation of further appliances within the dwelling (e.g., illumination and the like).

SUMMARY AND DESCRIPTION

The scope of the present invention is defined solely by the appended claims and is not affected to any degree by the statements within this summary.

Due to the ever increasing proportion of elderly persons in society and the increasing life expectancy, a system that enables people requiring care to be cared for effectively like an outpatient in their own dwelling is provided.

One or more of the present embodiments provide a modular assistance system for a person. The modular assistance system includes at least one mobile unit that has a recognition module for recognizing a functional requirement of the person and provides the corresponding function to the respective person depending on the detected functional requirement of the person using at least one interchangeable function module.

In one embodiment of the modular assistance system, the mobile unit has a housing on which and/or in which a plurality of interchangeable function modules are situated.

In one embodiment of the modular assistance system, the interchangeable function modules of the mobile unit are preconfigured in accordance with a physical condition of the person.

In a further embodiment of the system, the function modules of the mobile unit include at least one supply module for storing, preparing and/or supplying foodstuff and/or liquids and/or medicaments for the person.

In a further embodiment of the modular assistance system, the function modules of the mobile unit include at least one interface module for entering commands by the person or for outputting information to the person and/or to a remote monitoring station.

In a further embodiment of the modular assistance system, the function modules of the mobile unit include at least one cleaning module for cleaning a surface within a dwelling of the person and/or for cleaning the person themselves.

In a further embodiment of the modular assistance system, the function modules of the mobile unit include at least one measurement module for measuring bodily functions of the person and/or for measuring substances taken by the person.

In a further embodiment of the modular assistance system, the function modules of the mobile unit include at least one disposal module for disposing used articles of daily use, waste and/or bodily excrements from the person.

In a further embodiment of the modular assistance system, the function modules of the mobile unit include at least one sensor module for detecting a position and/or the positioning of the person and/or a hand position of the person.

In a further embodiment of the modular assistance system, the function modules include at least one controllable tablet module that may be moved automatically depending on the detected position or positioning relative to the appliance, and interchanges objects with further function modules of the mobile unit or a stationary unit using a controllable transportation unit.

In a further embodiment of the modular assistance system, the function modules include at least one appliance control module for controlling appliances within a dwelling of the person.

In a further embodiment of the modular assistance system, a stationary unit is provided in a dwelling of the person. The stationary unit charges a battery of the mobile unit and/or automatically fills supply containers of the supply modules or of the cleaning modules and/or automatically empties disposal containers of the disposal modules.

In a further embodiment of the modular assistance system, the function modules of the mobile unit include at least one drive module for driving the mobile unit and/or a piece of furniture for sitting and/or a piece of furniture for lying of the person.

In a further embodiment of the modular assistance system, the mobile unit includes a data processing unit that evaluates the data, provided by a measurement module, with respect to bodily functions of the person and/or the substances taken by the person and, depending on the evaluation result and/or depending on a physical condition of the person stored in a data storage medium, actuates a supply module, a communication module, a tablet module, an appliance control module, a drive module of the mobile unit, or any combination thereof, and/or provides information of the current state of the person to the person, to a care attendant, to a monitoring station via an interface module of the mobile unit, or any combination thereof.

In a further embodiment of the modular assistance system, the functions provided by the function modules of the mobile unit are also logged for evaluation by a care attendant and/or reported to a stationary unit of the modular assistance system and/or to a remote monitoring station via an interface module of the mobile unit.

DETAILED DESCRIPTION

Figure 1:
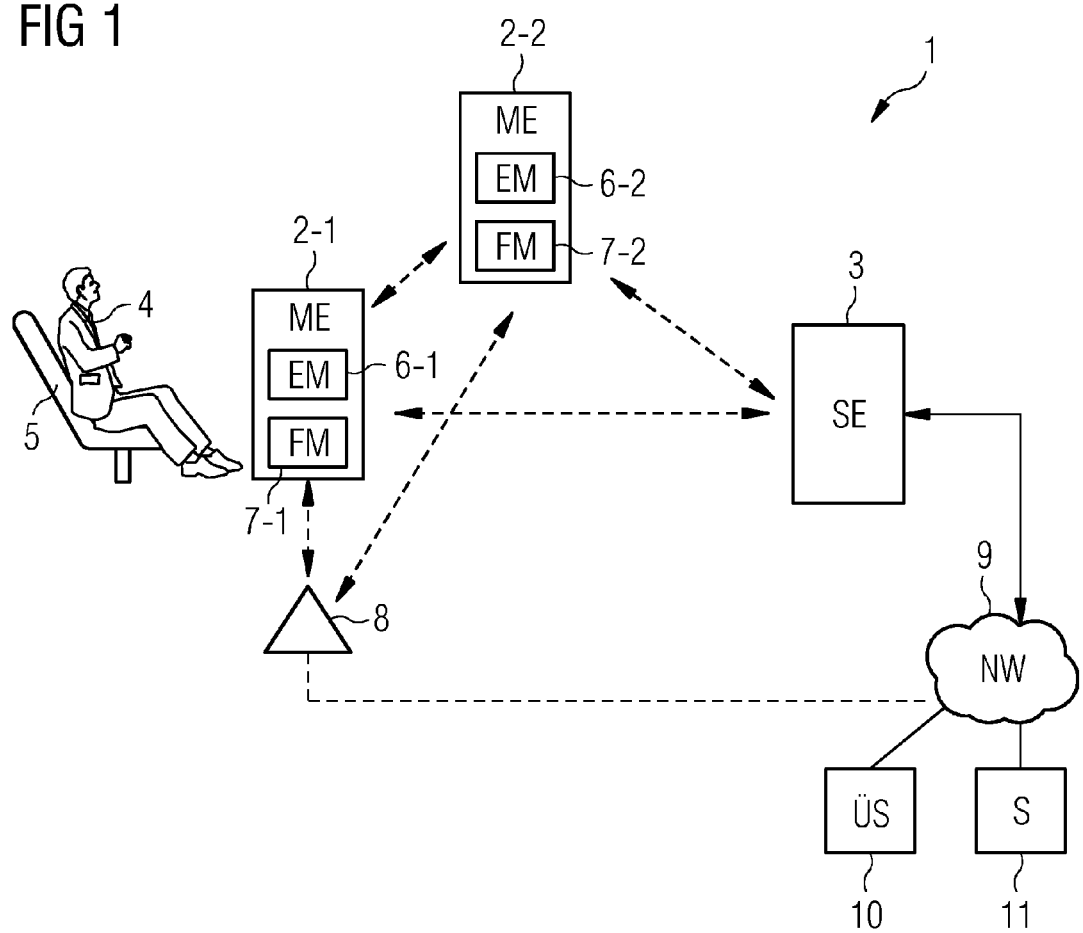
FIG. 1 shows a block diagram for an exemplary embodiment of a modular assistance system.

FIG. 1 shows one embodiment of a modular assistance system 1 that includes at least one (e.g., two) mobile units 2-1, 2-2 that may move (e.g., in the dwelling of a person 4 in need of assistance or to be cared for). In the exemplary embodiment of the modular assistant system 1 depicted in FIG. 1, the system 1 includes two mobile units 2-1, 2-2 that may communicate with one another via a wireless interface and may also interchange data in a bidirectional manner with a stationary unit 3. In a further embodiment of the modular assistance system 1, only one mobile unit 2 is provided. As shown in FIG. 1, the person 4 in need of assistance or to be cared for is seated on a piece of furniture for sitting 5. The piece of furniture for sitting 5 may also be a chair or a movable wheelchair or the like. The mobile units 2-1, 2-2 each have a recognition module 6-1, 6-2 for recognizing a functional requirement of the person 4. Each of the two mobile units 2-1, 2-2, respectively, has a plurality of interchangeable preconfigured function modules 7-1, 7-2 that provide the corresponding function to the respective person 4 depending on the functional requirement. The two mobile units 2-1, 2-2 may communicate with one another via a transceiver and a wireless interface. By way of example, the recognition module 6-1 may be situated in the vicinity of the person 4 and identify a functional requirement of the person 4. The recognition module 6-1 may report the identified functional requirement to the other mobile unit 2-2 and, optionally, to the stationary unit 3 of the modular assistance system 1. If the mobile unit 2-1 has a suitable function module 7 available, the mobile unit 2-1 may fulfill the detected functional requirement of the person 4 using the function module 7.

In one embodiment, the recognition module 6-i includes one or more sensors for detecting the position of the person 4 within the room or within a dwelling. In one embodiment, the position of a limb or a hand of the person 4 may be detected by the recognition module 6-i in three dimensions. In one embodiment, the recognition module 6-i is able to detect position and alignment of the piece of furniture for sitting or lying 5 of the person 4. In a further embodiment, the recognition module 6-i may verify (e.g., using speech analysis) whether the person 4 is a specific person. In one embodiment, this occurs by evaluating an acoustic signal, received from the person, based on parameters that are extracted from the signal. In this embodiment, the recognition module 6-i therefore includes a unit for person identification in order to determine which person 4 this is. The recognition module 6-i may also recognize commands from the person 4 (e.g., using speech analysis) or have an input unit.

In one embodiment of the modular assistance system 1, each mobile unit 2-i has a housing on which or in which a plurality of interchangeable function modules 7 are situated. These interchangeable function modules 7 may be situated within a housing of the mobile unit 2-i and may be interchanged by an operator or care attendant (e.g., after opening a flap or the like). Therefore, the function modules 7 may easily be interchanged manually by an operator. In a further embodiment, one or more function modules 7 are fastened to the housing of the mobile unit 2-i. The mobile unit 2-i, for example, includes docking stations for docking function modules 7. The mobile unit 2-i includes a plurality of different function modules 7 with different function module types. The different function module types are compiled by a care attendant in accordance with the needs of the person 4 to be cared for. The interchangeable function modules 7 of the mobile unit 2-i may be individually preconfigured in accordance with a physical condition of the person 4. In one embodiment, the interchangeable function modules 7 are embodied such that the interchangeable function modules 7 fit in an interlocking manner into corresponding compartments of the mobile unit 2-i and are able to latch in the corresponding compartments. The types of function modules 7 may be flexibly combined by a care attendant. As a result, the mobile unit 2 includes different onboard functionalities. In one embodiment, the mobile unit 2-i may move independently within a dwelling of the person 4 to be cared for. The mobile unit 2-i may autonomously avoid collisions with objects (e.g., dwelling walls or furniture). The mobile unit 2-i may independently follow the user or the person 4 to be cared for. By way of example, this is brought about via attaching an appropriate transceiver to the person 4. The transceiver reports the current position of the person 4 to the mobile unit 2-i. In a further embodiment, the mobile unit 2-i includes appropriate sensors of the recognition module 6 in order to detect the position and positioning of the person 4 in three dimensions. The mobile unit 2-i is able to move appropriately in relation to the identified positioning and position of the person 4 to be cared for and, for example, positions itself next to the person 4 for providing functions.

In one embodiment, the mobile unit 2-i includes supply modules VM that are provided for storing, preparing and supplying foodstuff and/or drinks. The mobile unit 2-i may also include function modules 7 that provide medicaments for the person 4. The supply modules VM may also include independent supply containers for food, liquid or the medicaments. In one embodiment, these supply containers may be refilled by a care attendant when necessary. In an alternative embodiment, the supply containers of the supply modules VM are refilled automatically by the stationary unit 3 when necessary. The mobile unit 2-i moves toward the stationary unit 3 in the dwelling and, when necessary, fills the supply containers for the various supply modules VM from storage containers of the stationary unit 3. In one embodiment, the mobile unit 2-i includes a preparation apparatus for preparing foodstuff or liquid for the person 4 to be cared for. By way of example, this preparation apparatus may prepare coffee, hot chocolate, tea or fruit juices (e.g., from concentrate or from standardized coffee pods) that are then provided for to person 4 (e.g., via a tablet). By way of example, the preparation apparatus may reheat meals prepared in advance when necessary. In one embodiment, the foodstuff or drinks situated in the storage containers are chilled in an appropriate function module 7. A further application example for the preparation of foodstuff lies in baking bread or pizza pieces or the like. The function module 7, which is provided for storing foodstuff or drinks, may, for example, have a chilled compartment, a freezer compartment or an option for dry storage. Provision may also be made for a storage container for hot water and a storage container for fresh water. Such a function module 7 may also have storage containers for consumables (e.g., paper towels or serviettes). Specific function modules 7 may be provided with storage options for articles of daily use such as, for example, a cellular telephone, a remote control, spectacles or a hearing aid. Function modules 7 may also be provided with storage containers for specific medicaments of the mobile unit 2-i. For example, the medicaments situated in the storage containers are tailored to the physical condition of the person 4. In one embodiment, the supply modules VM locally report when the supply modules VM have to be refilled to a control unit of the mobile unit 2-i. By way of example, a need for refilling may be identified by appropriate sensors or calculated from the amount of the dispensed stores. By way of example, this notification of required refilling may be transmitted by the mobile unit 2-i to the stationary unit 3 depicted in FIG. 1. The mobile unit 2-i may thereupon move toward the stationary unit 3 and, when there, reload or refill the required liquids, foodstuff or medicaments. Alternatively, the notification of required refilling may also be transmitted to a care attendant, who manually refills the appropriate containers at the next visit by the person 4 to be cared for. The mobile unit 2-i may also transmit the notification of requirements via a wireless interface to a transceiver or access point 8 situated in the dwelling. The transceiver or access point transmits the notification of requirements via a network 9 to a monitoring station 10 and, optionally, to a server 11. In one embodiment, the stationary unit 3 is also connected to the network 9. By way of example, the network 9 may be a public telephone network or the Internet. Independent of the notification of requirements, a care attendant may also be correspondingly informed so as to fill the storage containers when necessary.

Figure 2:
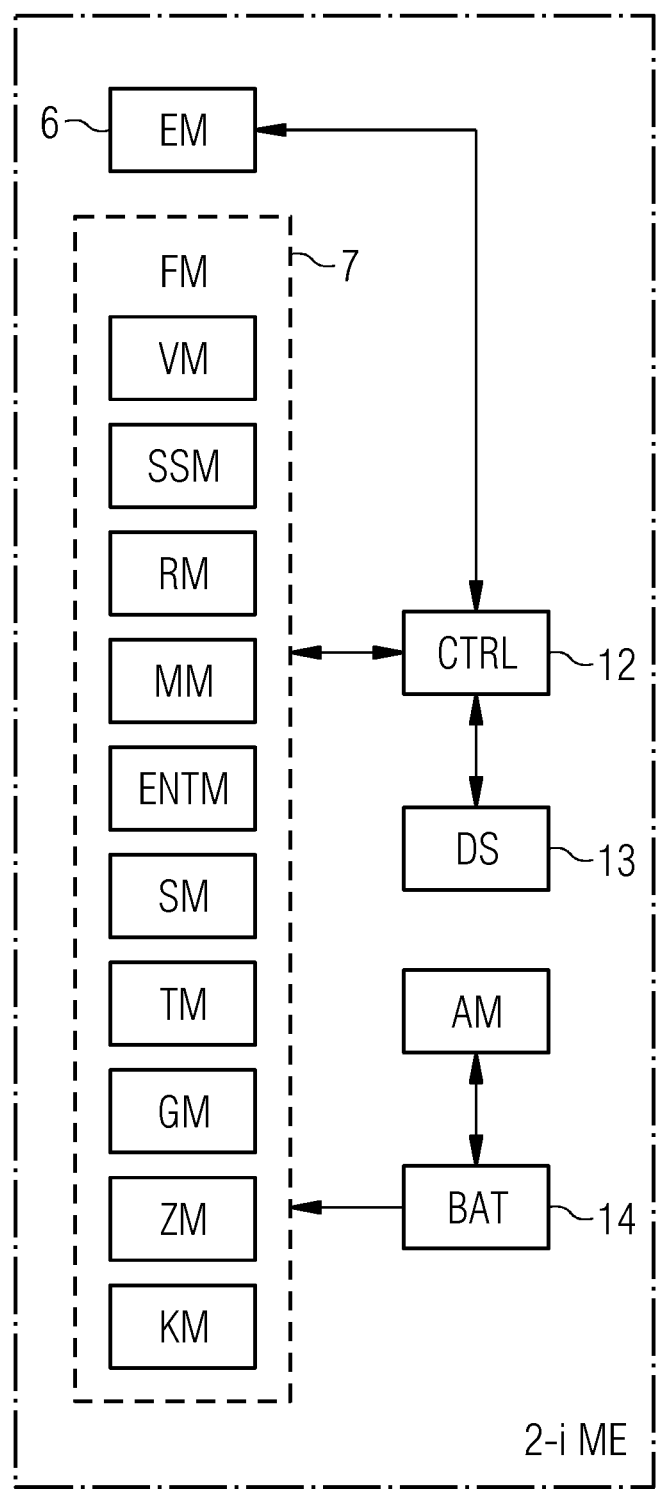
FIG. 2 shows a block diagram for an exemplary embodiment of a mobile unit within the modular assistant system.

The mobile unit 2-i may have different styles or types of function modules 7. FIG. 2 shows a block diagram of an embodiment of a mobile unit 2-i that, in addition to one or more recognition modules 6, includes different types of function modules 7.

FIG. 2 shows that the mobile unit 2-i has at least one supply module VM for storing, preparing or supplying foodstuff as a function module 7. Modules for the provision of medicaments for the person 4 may be provided as function modules 7.

The function modules 7 also include interface modules SSM for entering commands by the person 4 or for outputting information to the person 4. The interface modules SSM may be provided for transmitting information or notifications to a remote monitoring station 10 or a remote server 11. The interface modules SSM may also transmit information or notifications to a reception unit of an operator or care attendant.

Communication modules KM may establish communication connections (e.g., to the Internet, to a telephone network or to a central call center) and provide monitoring and alarm functions.

The function modules 7 may include one or more cleaning modules RM for cleaning a surface within a dwelling of the person and cleaning modules RM for cleaning the person themselves.

The function modules 7 have one or more measurement modules MM that include for measuring bodily functions of the person or for measuring substances taken by the person 4. By way of example, a measurement module MM may monitor the heart beat of the person 4 via electrodes. A further example is a measurement module MM for measuring the blood pressure of a person 4. A measurement module MM for measuring a blood count of the person 4 may also be provided. The measurement modules MM may also monitor the substances taken by the person 4. For example, the measurement modules MM may monitor and record the type and amount of medicaments taken by the person 4. The measurement modules MM may also detect the foodstuff and drinks taken by the person 4. This allows an operator or care attendant, who visits the person 4 to be cared for in their dwelling, to easily determine whether the person 4 has taken enough drinks or foodstuff. In one embodiment, the measured data may be reported via the network 9 to a remote monitoring station 10. This enables remote monitoring of the physical condition of the person 4 to be cared for. The person 4 may read the corresponding information or measurement data via a display of a communication module KM.

In one embodiment, the function module includes disposal modules ENTM for disposing used articles of daily use and disposal modules ENTM for disposing bodily excrements from the person 4. By way of example, a dish rack for used dishes (e.g., cups, glasses or plates) may be provided for in the mobile unit 2. Used dishes are temporarily stored in the dish rack and may be cleaned in a dishwasher. Disposal modules ENTM for disposing waste (e.g., used paper handkerchiefs and the like) may also be provided.

The mobile unit 2 may provide one or more sensor modules SM for detecting a position or positioning of the person 4 or a hand of the person 4 as function modules 7. The sensor module SM may also be integrated into the recognition module 6. The sensor module SM may also be configured to identify or authenticate the person 4.

In a further embodiment of the system, the function modules 7 include at least one controllable tablet module TM that may be moved automatically to the suitable position depending on the detected position or positioning of the person 4. The tablet or table module TM may provide drinks and meals for the person 4. The tablet module TM, for example, has a controlled robot arm or the like. Attached to the tablet module there may be optional keys or other operating elements, which, optionally, form an additional input module EM.

The function modules 7 of the mobile unit 2 may also have one or more appliance control modules GM for controlling appliances within the dwelling of the person 4. By way of example, the appliance control modules GM may actuate a remote-controlled vacuum cleaner within the dwelling. In one embodiment, the appliance control module GM is controlled by the person 4 to be cared for (e.g., using an appropriate interface). This enables the person 4 to be cared for to assist in the cleaning of the dwelling. The appliance control modules GM may also actuate further appliances within the dwelling (e.g., illumination, blinds or the like).

As further function module 7, the mobile unit 2-i includes at least one drive module AM for driving the mobile unit 2-i within the dwelling. Drive modules AM for moving a piece of furniture 5 for sitting or lying of the person 4 may also be provided. By way of example, the mobile unit 2-i may include a docking station for docking to the piece of furniture 5 for sitting of the person 4. The piece of furniture 5 for sitting may be moved within the dwelling with the aid of the drive module AM in accordance with the wishes of the person 4. By way of example, the occupant or the person 4 to be cared for may be driven to another room within the dwelling with the aid of such a drive module AM. In a further embodiment, the mobile unit 2 includes an independent seating module that may also help the person with standing up.

FIG. 2 also shows that the mobile unit 2-i includes a control or an integrated data processing unit 12 that also has access to a local data storage medium 13. Configuration data may be situated in the data storage medium 13. In one embodiment, data reproducing the physical condition of the person 4 to be cared for are stored in the data storage medium 13. A diagnosed disease or the like may be stored in the data storage medium 13 and may be called by the data processing unit 12. In one embodiment, the data processing unit 12 evaluates the data, provided by a measurement module MM, with respect to bodily functions of the person 4 or with respect to substances taken by the person 4, and actuates one or more supply modules 7 depending on an evaluation result and possibly depending on information data relating to the physical condition of the person 4 read from the data storage medium. By way of example, the control apparatus or the data processing unit 12 may control supply modules VM, communication modules KM, the tablet module TM or an appliance control module GM, and a drive module AM of the mobile unit 2 in accordance with the evaluation result. The control apparatus or the data processing unit 12 may also inform the person 4 themselves or a care attendant or a remote monitoring station about the current state of the person 4 via an interface module SSM of the mobile unit 2. The functions provided by the function modules 7 of the mobile unit 2 may be logged for subsequent evaluation by a care attendant or reported to the stationary unit 3 of the modular assistance system 1 or, additionally, to a remote monitoring station 10 via an interface module SSM of the mobile unit 2. Depending on the application, separately described function modules 7 may also be integrated into one module. In one embodiment, function modules 7 currently not required may be parked in one or various park apparatuses within a room of the dwelling (e.g., a preparation module ZM may be parked in a park apparatus installed in the kitchen).

FIG. 2 shows that the mobile unit 2 includes at least one battery 14 that supplies the various modules of the mobile unit 2 with power and, for example, supplies power for the drive modules AM of the mobile unit 2-i. In one embodiment, the battery 14 is recharged by the stationary unit 3, when required, when the mobile unit 2 docks onto the stationary unit 3.

Figure 3:
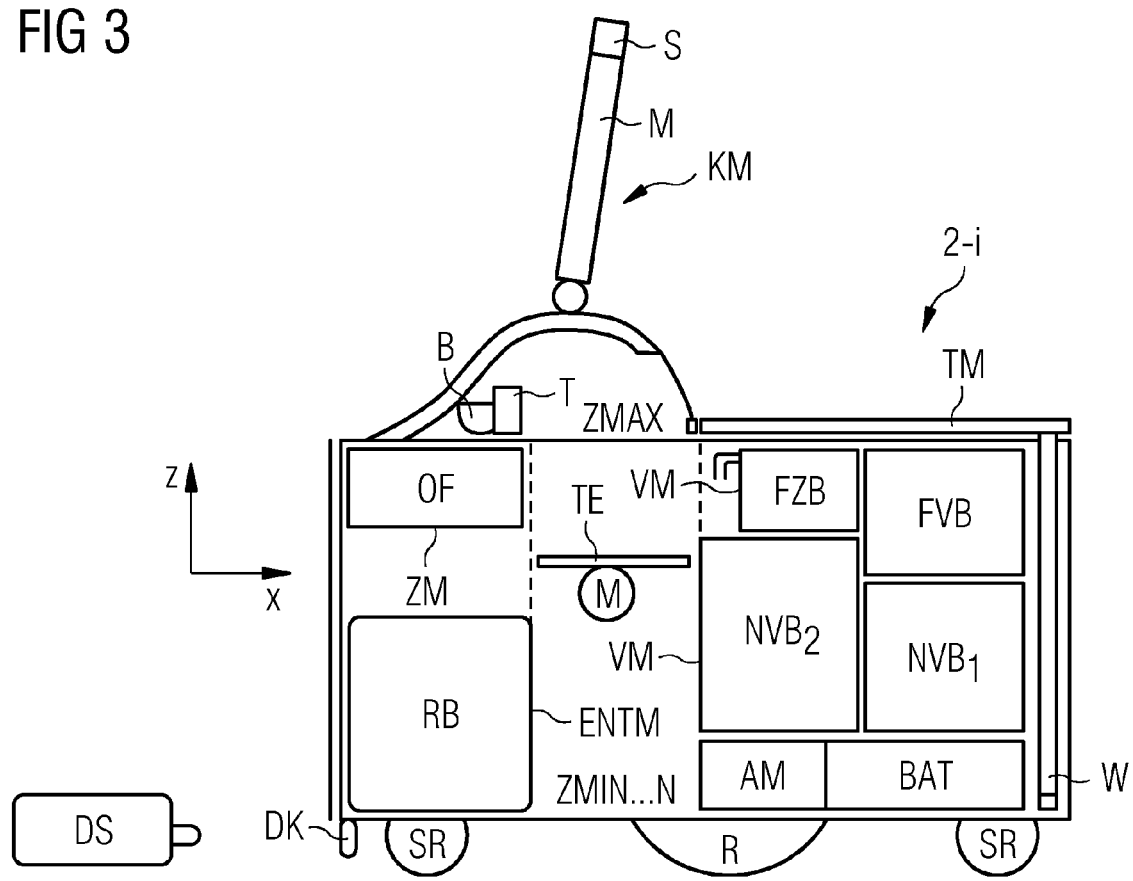
FIG. 3 shows a sectional view through a mobile unit in accordance with an exemplary embodiment of the assistance system.

FIG. 3 shows a sectional view through one embodiment of a mobile unit 2-i of the modular assistance system 1.

FIG. 3 shows that the mobile unit 2-i includes a housing, in which a plurality of function modules 7 of different types may be situated. In the example shown in FIG. 3, a transportation unit TE is provided in the housing of the mobile unit 2-i. The transportation unit TE may move in the vertical direction in a transportation shaft using an electric motor. The transportation unit TE also includes a platform that may move horizontally. The transportation unit TE may be moved between a base of the housing and an opening of the housing, which is situated level with the tablet of a tablet module TM. The transportation unit TE may be moved in the Z-direction between a lowermost position $Z_{min}$ and a highest position $Z_{max}$.

The transportation unit TE is actuated by the control apparatus 12 of the mobile unit 2.

The transportation unit TE forms an internal tablet of the mobile unit 2 and primarily serves for supplying the person 4 with drinks and foodstuff. In the depicted exemplary embodiment, the mobile unit 2 includes a liquid supply container FVB (e.g., a water tank) that is chilled in one embodiment. In the depicted exemplary embodiment, this water tank or liquid supply container is connected to a liquid preparation unit FZB that, for example, heats water. The supply container and the preparation unit FZB form a supply module VM of the mobile unit 2-i.

In the depicted exemplary embodiment, the mobile unit 2-i includes a supply container for foodstuff (e.g., a foodstuff supply container NVB1). Premade meals or ready meals may be stored chilled in this container NVB. Additionally, a further foodstuff supply container NVB2 that is not chilled may be provided. The supply container for the foodstuff forms a further supply module VM of the mobile unit 2-i. The mobile unit 2-i has a returns container RB as a disposal module ENTM. Within the mobile unit 2, a stove OF (e.g., an oven OF) that serves as preparation module ZM may also be provided. Beakers B and cups T may be stored in one area of the mobile unit 2, as shown in FIG. 3.

In the exemplary embodiment shown, the mobile unit 2-i has a battery BAT for supplying the function modules 7 with power. A drive wheel R is driven by a wheel-hub motor. The mobile unit 2-i also has support wheels SR. A docking contact DK may be docked onto a docking station DS when necessary, for example, to recharge the battery BAT again. In the example shown, the tablet module TM may also include a weighing apparatus W in order, for example, to monitor the amount of foodstuff or drinks supplied. As shown in FIG. 3, a communication module KM, which includes a monitor M and an appropriate sensor system S (e.g., microphones or the like) may be provided on the housing of the mobile unit 2-i. By way of example, function procedures may be controlled by voice control. By way of example, if a person 4 wishes to obtain a hot drink, the person may communicate this desire to the control unit 12 within the mobile unit 2-i via the communication module KM.

Figure 7A:
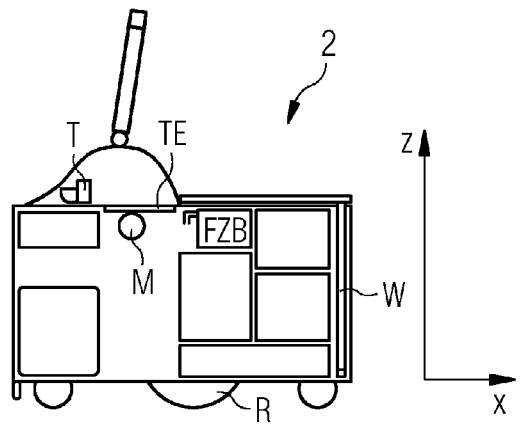
FIGS. 7A-7F show sectional views through a mobile unit for depicting a filling procedure of a glass for explaining the functionality of the mobile unit in an embodiment of the modular assistance system.
Figure 7B:
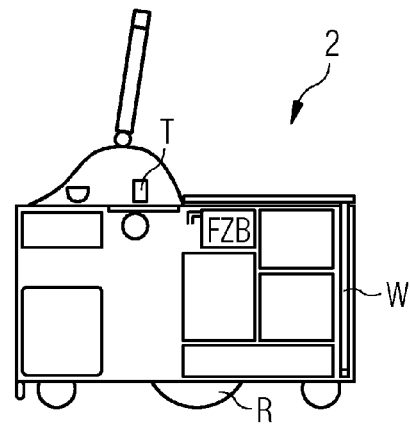
Figure 7C:
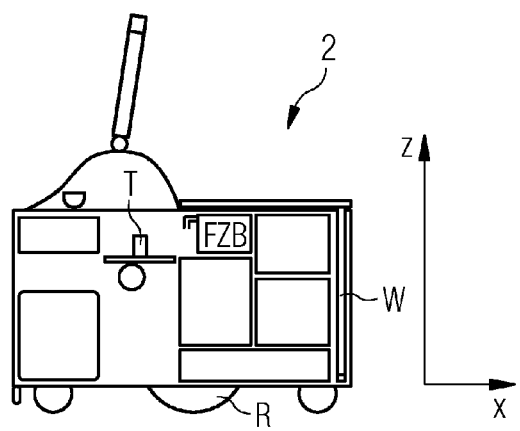
Figure 7D:
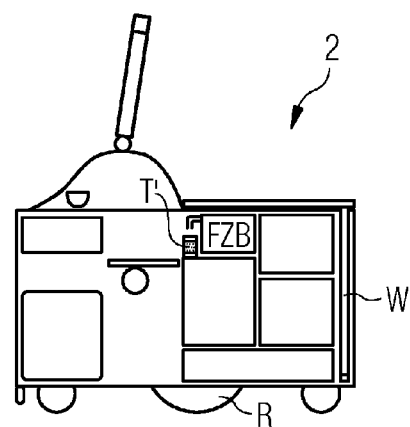
Figure 7E:
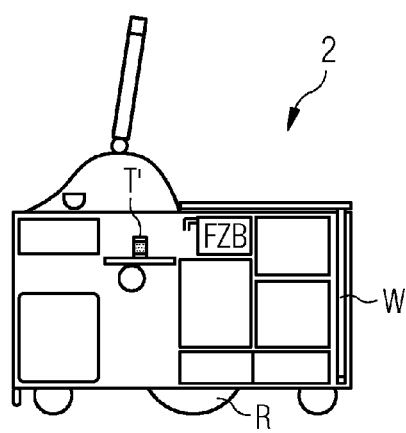
Figure 7F:
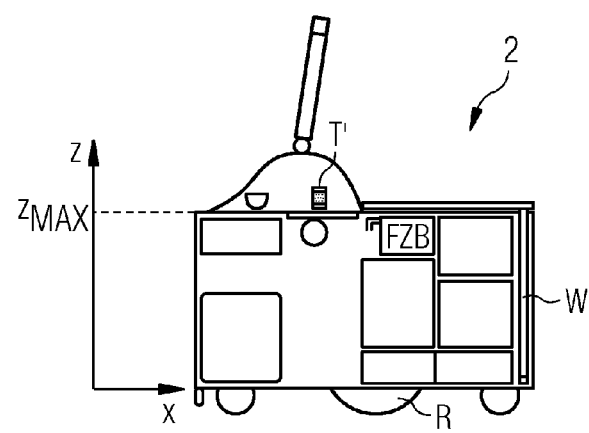

FIGS. 7A to 7F show for the exemplary embodiment of a mobile unit 2 depicted in FIG. 3 how a corresponding drink is prepared and supplied to the person 4 in accordance with the expressed desire. FIG. 7A shows the initial state, in which the cup T is ready at the upper end of a vertical transportation shaft. The transportation unit TE is moved into the maximum position $Z_{max}$, and the cup T is pushed onto the tablet of the transportation unit TE by a pusher. The empty cup T is subsequently brought within the transportation shaft into the upper final position at a specific level, corresponding to a filling area in front of the drinks preparation unit FZB, by the transportation unit TE. The cup, which is still empty, is pushed in front of the drinks preparation unit FZB and is filled there, as depicted in FIG. 7D. The filled cup T' of tea is pushed back onto the tablet of the transportation unit TE, as depicted in FIG. 7E. Subsequently, the transportation unit TE once again moves within the supply shaft or transportation shaft into the upper maximum position $Z_{max}$, as depicted in FIG. 7F, and is subsequently pushed onto the tablet of the tablet module TM. Optionally, the scales W of the tablet module TM check whether or not the cup T' is sufficiently filled. In one embodiment, the cup T' is, in accordance with a detected hand position of the person 4, pushed onto the tablet of the tablet module TM such that the person 4 to be cared for may pick the cup T' up without difficulties, for drinking. In one embodiment, the person 4 may also correct or control the transportation of the cup T' by entering appropriate speech commands. In the embodiment shown in FIG. 3, the mobile unit 2-i includes a transportation shaft, in which an integrated transportation unit TE may move in the Z-direction. In one embodiment, the mobile unit 2-i may include more than one transportation shaft. In the embodiment shown in FIG. 3, the mobile unit 2-i includes a plurality of different function modules 7 of different types that may, for example, be latched into appropriate insertion compartments and, when necessary, be interchanged by an operator. In the depicted example, supply modules VM supply prepared drinks or foodstuff to the person 4. By way of example, foodstuff or a premade meal may be heated by the oven OF as preparation module ZM and supplied to the person 4 by the transportation unit TE. The used cup may be transported by the transportation unit TE to the returns container RB as disposal module ENTM and unloaded there. The function modules 7 integrated in the housing of the mobile unit 2-i may be interchanged on a modular basis by an operator. The function modules 7 are tailored to the individual needs of the person. The various function modules 7 are tailored to the individual physical condition of the person 4, or preconfigured accordingly. By way of example, the mobile unit 2-i may also include supply containers for medicaments or the like. The medicaments are preconfigured for the respective physical state of the person 4. The provided medicaments may include, for example, tablets, pills, electrolytes and the like.

Figure 4:
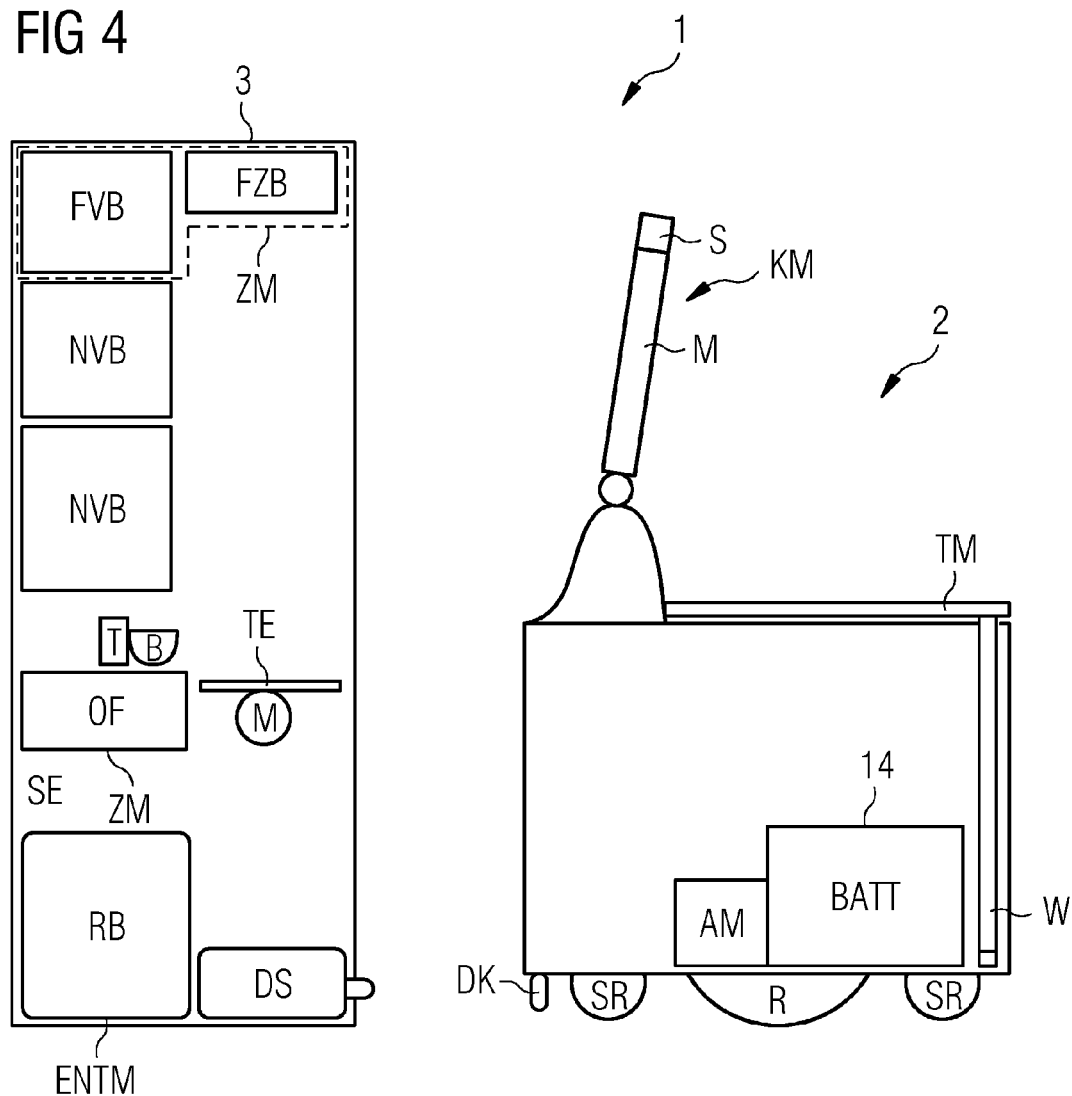
FIG. 4 shows a sectional view through a stationary unit and a mobile unit in accordance with an exemplary embodiment of the modular assistance system.
Figure 5:
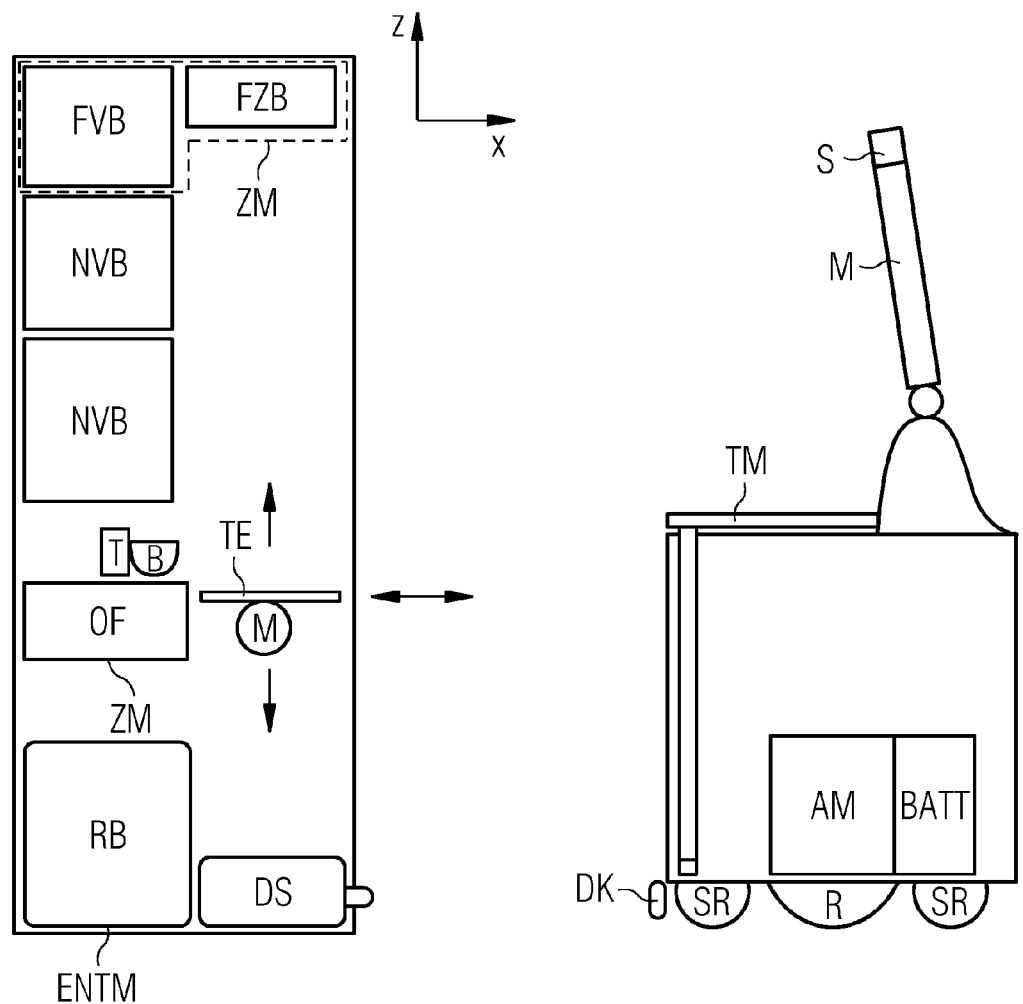
FIG. 5 shows a further sectional view of an exemplary embodiment of the modular assistance system.

In the embodiment shown in FIG. 4, the supply modules VM are situated in a stationary unit 3, and the mobile unit 2 is configured to transport the already prepared meals and drinks, and to provide the already prepared meals and drinks to the person 4 to be cared for. In this embodiment, a transportation unit TE is situated within a transportation or supply shaft of the stationary unit 3 and, for example, pushes a cup T or a beaker B with a drink onto a tablet of the tablet module TM of the mobile unit 2. The mobile unit 2 subsequently drives from the stationary unit 3 toward the detected position of the person 4 to be cared for and provides the prepared drink or the cup T to the person 4 in accordance with the detected position or hand position of the person. In the embodiment shown in FIG. 4, the mobile unit 2 does not include supply modules, but includes communication modules KM and interface modules SSM and the like. The battery 14 of the mobile unit 2 is once again recharged, when necessary, via a docking contact DK on a docking station DS of the stationary unit 3. In one embodiment, the mobile unit 2 may independently rotate for holding drinks or prepared meals such that the tablet of the tablet module TM faces the stationary unit 3, as shown in FIG. 5. After the cups T or beakers B or plates were pushed onto the tablet of the tablet module TM of the mobile unit 2-i, the mobile unit 2 subsequently moves to the position of the person 4 to be cared for. The embodiment shown in FIGS. 4 and 5 offers the advantage that more space is available for the storage containers, for the foodstuff and drinks or other objects than in the embodiment shown in FIG. 3, in which all function modules 7 are provided within the housing of the mobile unit 2. In one embodiment, the variants of FIG. 3 and FIG. 4 may be combined with one another (e.g., some of the function modules 7 are situated in the stationary unit 3 and other function modules 7 are situated within the housing of the mobile unit 2-i). Both the stationary unit 3 and the mobile unit 2 include their own integrated transportation unit TE within a transportation shaft. The stationary unit 3 shown in FIG. 4 may be connected to a server 11 or a monitoring station 10 via a network 9. When necessary, this may be used to request refilling of the supply containers within the stationary unit 3.

Figure 6:
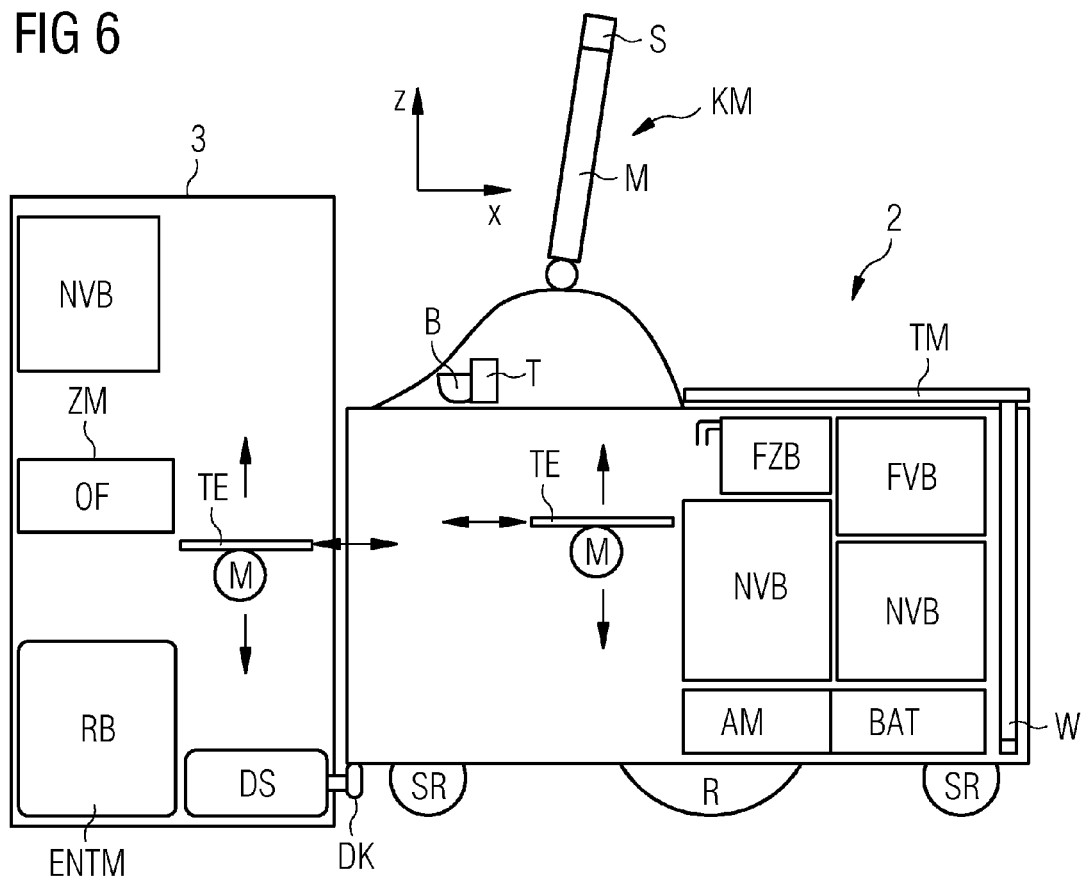
FIG. 6 shows a sectional view through a stationary unit and a mobile unit, docked on the stationary unit, in accordance with an exemplary embodiment of the modular assistant system.

FIG. 6 shows an embodiment, in which both the stationary unit 3 and the mobile unit 2 include a transportation unit TE. The tablets of the two integrated transportation units TE may be moved to the same level such that cups T, plates or the like may be pushed in a desired direction between the tablet of the transportation unit TE in the stationary unit 3 and the tablet of the transportation unit TE in the mobile unit 2, as required. Meals and drinks may be prepared either in the stationary unit 3 or in the mobile unit 2. By way of example, in the exemplary embodiment depicted in FIG. 6, meals are prepared within the stationary unit 3 by an oven OF, whereas drinks are prepared by a liquid preparation unit FZB within the mobile unit 2.

The modular assistant system 1 according to one or more of the present embodiments has a number of advantages. The modular assistant system 1 allows larger time intervals between the visits of the person 4 to be cared for by the care attendants. In the time intervals between the visits by the care attendants, the person 4 may independently initiate the provision of functions and need not wait for the care attendant in each case. In accordance with physical condition and capabilities, the person 4 to be cared for may define the scope of functions, which is provided for by the mobile unit 2, and extend the mobile unit 2 when necessary. The person 4 to be cared for is to learn the manipulation of the control of a single appliance in order to have a number of very different functions provided. The supply with drinks and liquids and the monitoring of the physical state of the person 4 may be brought about by the mobile unit 2, reducing risks to health. By way of example, diabetics obtain meals suitable for them. Handling of the mobile unit 2 is practical for and may easily be learned by the person 4 to be cared for. One or more of the present embodiments offer a mobile platform with a modular configuration and a comprehensive scope of functions. The mobile platform is individually tailored to the capabilities and the physical state of the person 4. Errors that may impair or pose a risk to the health of the affected person are avoided with great reliability. The independence of the person 4 to be cared for is significantly increased, and hence, there is a substantial reduction in the dependence on a care attendant. Even persons 4 with restricted mental and physical abilities may therefore be reliably cared for in their dwelling without restricting their quality of life (e.g., without requiring the constant presence of a care attendant). In further embodiment, further functions may be made available to the person 4 (e.g., a scheduling function for planning the daily routine such as times for main meals or reminder notifications for taking medicaments and the like). Further communication links may also be provided (e.g., communication links to the Internet or to a telephone network or a call center). The communication module KM may also be provided for entertaining the person (e.g., providing television images or a radio or a stereo system). The mobile unit 2 allows the person to be cared for to undertake activities within the dwelling itself (e.g., by controlling a vacuum cleaner that may also be integrated in the mobile unit 2). The modular assistance system 1 may include a plurality of mobile units 2 that may communicate with one another). Thus, for example, a mobile unit 2-1 may be used to supply the person 4 with drinks or foodstuff, while another mobile unit 2-2 is provided for disposal. The modular assistance system 1 according to one or more of the present embodiments may, for example, be used for caring for any person 4, with it being suitable, for example, for caring for relatively old persons 4 in need of care.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims can, alternatively, be made to depend in the alternative from any preceding or following claim, whether independent or dependent, and that such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A modular assistance system for a person, the modular assistance system comprising:
   at least one mobile unit comprising a recognition module, the recognition module configured for detecting a functional requirement of the person;
   a plurality of interchangeable function modules, wherein the at least one mobile unit is configured to provide a corresponding function to the respective person in response to the detected functional requirement of the person, using at least one interchangeable function module of the plurality of interchangeable function modules, and wherein the at least one interchangeable function module comprises at least one controllable tray module including a tray, the at least one controllable tray module being automatically movable in response to the detected functional requirement of the person and operable to interchange objects with function modules of the at least one mobile unit or a further stationary unit using a controllable transportation unit, and wherein the controllable transportation unit is movable in a transportation shaft of the at least one mobile unit; and
   a processor and a memory in communication with the processor, the memory configured to store information data relating to a condition of the person, the processor configured to activate one or more interchangeable function modules of the plurality interchangeable function modules based on the condition of the person.

2. The modular assistance system of claim 1, wherein the mobile unit comprises a housing for receiving the plurality of interchangeable function modules.

3. The modular assistance system of claim 2, wherein the plurality of interchangeable function modules of the mobile unit are preconfigured in accordance with a physical condition of the person.

4. The modular assistance system of claim 1, wherein the recognition module further comprises at least one sensor module operable for detecting a position of the person, positioning of the person, detecting a position of a hand of the person, positioning of the hand of the person, or a combination thereof.

5. The modular assistance system of claim 1, wherein the plurality of interchangeable function modules further comprises at least one supply module operable for storing, preparing, and supplying foodstuff, liquids, medicaments, or any combination thereof for the person, or any combination thereof.

6. The modular assistance system of claim 1, wherein the plurality of interchangeable function modules further comprises at least one interface module operable for entering commands by the person or for outputting information to the person, to a remote monitoring station, or to the person and to the remote monitoring station.

7. The modular assistance system of claim 1, wherein the plurality of interchangeable function modules further comprises at least one cleaning module operable for cleaning a surface within a dwelling of the person, cleaning the person, or a combination thereof.

8. The modular assistance system of claim 1, wherein the plurality of interchangeable function modules further comprises at least one measurement module operable for measuring bodily functions of the person, measuring substances taken by the person, or a combination thereof.

9. The modular assistance system of claim 1, wherein the plurality of interchangeable function modules further comprises at least one disposal module operable for disposing used articles of daily use, waste, bodily excrements, or any combination thereof from the person.

10. The modular assistance system of claim 1, wherein the plurality of interchangeable function modules further comprises at least one appliance control module operable for controlling appliances within a dwelling of the person.

11. The modular assistance system of claim 1, further comprising a stationary unit provided in a dwelling of the person, the stationary unit operable to charge a battery of the at least one mobile unit, automatically fill supply containers of supply modules or of cleaning modules, automatically empty disposal containers of disposal modules, or any combination thereof.

12. The modular assistance system of claim 1, wherein the plurality of interchangeable function modules further comprises at least one drive module operable for driving the at least one mobile unit, a piece of furniture for sitting, a piece of furniture for lying of the person, or any combination thereof.

13. The modular assistance system of claim 1, wherein the data processor is further configured to:
   evaluate data, provided by a measurement module, with respect to bodily functions of the person, substances taken by the person, or a combination thereof; and
   depending on an evaluation result, a physical condition of the person stored in a data storage medium, or a combination thereof, actuate a supply module, a communication module, the tray module, an appliance control module, a drive module, a preparation module of the at least one mobile unit, or any combination thereof, report a current state of the person to the person, to a care attendant, to a monitoring station, or to any combination thereof via an interface module of the at least one mobile unit, or a combination thereof.

14. The modular assistance system of claim 1, wherein the function provided by the plurality of interchangeable function modules of the mobile unit is logged for evaluation by a care attendant, reported to a stationary unit of the modular assistance system, to a remote monitoring station via an interface module of the at least one mobile unit, or a combination thereof, or is logged and reported.

15. The modular assistance system of claim 3, wherein the plurality of interchangeable function modules comprises at least one supply module operable for storing, preparing, and supplying foodstuff, liquids, medicaments, or any combination thereof for the person, or any combination thereof.

16. The modular assistance system of claim 3, wherein the plurality of interchangeable function modules comprises at least one interface module operable for entering commands by the person or for outputting information to the person, to a remote monitoring station, or to the person and to the remote monitoring station.

17. The modular assistance system of claim 3, wherein the plurality of interchangeable function modules comprises at least one cleaning module operable for cleaning a surface within a dwelling of the person, cleaning the person, or a combination thereof.

18. A modular assistance system for a person, the modular assistance system comprising:
   at least one mobile unit comprising a compartment configured to interlock with at least one interchangeable function module of a plurality of interchangeable function modules;
   a recognition module, the recognition module configured for detecting a functional requirement of the person, the at least one mobile unit configured to provide a corresponding function to the person, depending on the detected functional requirement of the person, using the at least one interchangeable function module; and
   a processor and a memory in communication with the processor, the memory configured to store information data relating to a condition of the person, the processor configured to activate one or more interchangeable function modules of the plurality of interchangeable function modules based on the condition of the person.

19. A modular assistance system for a person, the modular assistance system comprising:
   at least one mobile unit comprising a drive module including a motor and at least one wheel, the drive module configured to propel the at least one mobile unit;
   a recognition module, the recognition module including a sensor configured for detecting a functional requirement of the person, the at least one mobile unit configured to provide a corresponding function to the respective person, depending on the detected functional requirement of the person, using at least one interchangeable function module of a plurality of interchangeable function modules; and
   a processor and a memory in communication with the processor, the memory configured to store information data relating to a condition of the person, the processor configured to activate one or more interchangeable function modules of the plurality of interchangeable function modules based on the condition of the person.

20. The modular assistance system of claim 19, further comprising:
   at least one battery configured to power the mobile unit and the at least one interchangeable function module; and
   a docking contact configured to dock into a docking station to charge the battery.

* * * * *